United States Patent [19]

Bauer

[11] Patent Number: 4,593,118

[45] Date of Patent: Jun. 3, 1986

[54] 2-AMIDO-3-AMINOCARBOXYLIC ACID ESTERS AND PROCESS OF PREPARATION THEREOF

[75] Inventor: Beverly A. Bauer, Baton Rouge, La.

[73] Assignee: Ethyl Corporation, Richmond, Va.

[21] Appl. No.: 708,893

[22] Filed: Mar. 6, 1985

Related U.S. Application Data

[63] Continuation-in-part of Ser. No. 563,704, Dec. 21, 1983, abandoned, and a continuation-in-part of Ser. No. 563,705, Dec. 21, 1983, abandoned, and a continuation-in-part of Ser. No. 563,706, Dec. 21, 1983, abandoned.

[51] Int. Cl.$^4$ .............. C07C 101/02; C07C 125/065
[52] U.S. Cl. ....................... 560/41; 560/27; 560/29; 560/32; 560/35; 560/38; 560/115; 560/168
[58] Field of Search ............. 560/41, 32, 168, 35, 560/38, 29, 27, 115

[56] References Cited

U.S. PATENT DOCUMENTS

| 2,844,630 | 7/1958 | Johnson et al. | 560/168 X |
| 3,215,730 | 11/1965 | Spathe et al. | 560/168 |
| 3,394,187 | 7/1968 | Markiewitz | 564/486 |

FOREIGN PATENT DOCUMENTS 45-3083 2/1970 Japan .

OTHER PUBLICATIONS

McCord et al., Jour. Med. Chem., vol. 10 (1967) 353–355.
Atherton et al., The Jour. of Antibiotics, vol. XXV No. 9 (1972) 539–540.
Atherton et al., H. S. Z. Physiol. Chem. vol. 354 (1972) 689–696.
Inoue, Bull. Chem. Soc. Japan, vol. 34 (1961) 885–886.
Albertson, Jour. Amer. Chem. Soc., vol. 70 (1948) 1150–1152.
Borch, Jour. Amer. Chem. Soc., vol. 93 (1971) 2897–2904.
Adkins, Jour. Amer. Chem. Soc., vol. 60 (1938) 1328–1331.
Adams, Organic Reactions, vol. 7 (1953) 327–341, 353, 354, 366–370 and 375–377.
Allinger, Organic Chemistry (1971) 532–537.
Neuberg, Chem. Zentr., vol. II (1906) 764–766.
Degering, Outline of Organic Nitrogen Compounds (1945) 192–193.
Organic Synthesis, vol. 5 32–35 and 373–375.
The Peptides, vol. 3, Academic Press, New York, especially pp. 7–49 (1981).
Organic Syntheses, Collective vol. 3, John Wiley & Sons, New York, pp. 501–502 and 717–719.

*Primary Examiner*—Bernard Helfin
*Attorney, Agent, or Firm*—Donald L. Johnson; John F. Sieberth; Patricia J. Hogan

[57] ABSTRACT

2,3-Diaminocarboxylic acid compounds are prepared by (A) nitrosating a β-keto ester to form a 3-keto-2-oximino ester, (B) converting the resultant oxime to a protected 2-amine, (C) reductively aminating the 3-position of the protected 2-amine to form a 2,3-diaminocarboxylic acid ester wherein the 2-amino group is protected, and (D) when desired, treating the 2,3-diaminocarboxylic acid ester to deprotect one or more of the amino and carboxyl groups.

12 Claims, No Drawings

2-AMIDO-3-AMINOCARBOXYLIC ACID ESTERS AND PROCESS OF PREPARATION THEREOF

CROSS-REFERENCE TO RELATED APPLICATIONS

This application is a continuation-in-part of copending applications Ser. Nos. 563,704, 563,705, and 563,706, all filed Dec. 21, 1983, and now abandoned.

FIELD OF INVENTION

This invention relates to 2,3-diaminocarboxylic acid compounds and more particularly to processes for preparing them.

BACKGROUND

It is known that 2,3-diaminocarboxylic acid compounds are useful materials that find application, e.g., in the preparation of antibiotics. Various methods are known for the production of these compounds—2,3-diaminopropionic acid being synthesizable, e.g., by the rearrangement of aspartic acid, and higher 2,3-diaminocarboxylic acids being synthesizable, e.g., by the processes of Neuberg, *Chem. Zentr.*, II, (1906), pp. 764–766; Inoue, *Bull. Chem. Soc. Japan*, Vol. 34, (1961), pp. 885–886, and Japanese Patent Publication SHO 45 [1970]-3083; McCord et al., *Journal of Medicinal Chemistry*, Vol. 10, (1967), pp. 353–355; and Atherton et al., *The Journal of Antibiotics*, Vol. XXV, No. 9 (1972), pp. 539–540, and *H.S.Z. Physiol. Chem.*, Vol. 354, (1972), pp. 689–696. However, these known processes have certain disadvantages, viz.:

(1) the 2,3-diaminopropionic acid process is not adaptable to the preparation of higher 2,3-diaminocarboxylic acids,
(2) Neuberg's process provides a low yield of product,
(3) Inoue's process results in the formation of explosive intermediates,
(4) the process of McCord et al. does not permit the formation of 2,3-diaminocarboxylic acids having two free amino groups, and
(5) the process of Atherton et al. uses an expensive starting material and involves so many steps as to be a tedious process.

Thus, there is still a need for an economical, industrially attractive method of preparing 2,3-diaminocarboxylic acids containing more than three carbons.

SUMMARY OF INVENTION

An object of this invention is to provide a novel process for preparing 2,3-diaminocarboxylic acid compounds.

Another object is to provide such a process that is economical, industrially attractive, and adaptable to the preparation of 2,3-diaminocarboxylic acids containing more than three carbons.

A further object is to provide novel compounds useful in the preparation of 2,3-diaminocarboxylic acids.

These and other objects are attained by (A) nitrosating a β-keto ester to form a 3-keto-2-oximino ester, (B) converting the resultant oxime to a protected amine, (C) reductively aminating the 3-position of the protected amine, and (D) when desired, treating the resultant compound to deprotect one or more of the amino and carboxyl groups.

DETAILED DESCRIPTION

β-Keto esters useful as starting materials in the practice of the invention are generally compounds corresponding to the formula:

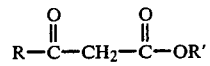

wherein R and R' are independently selected from alkyl, cycloalkyl, and aryl groups, generally such groups containing 1–10 carbons and preferably alkyl groups containing 1–6 carbons, such as methyl, ethyl, propyl, isopropyl, butyl, t-butyl, hexyl, etc. Exemplary of such compounds are the methyl, ethyl, t-butyl, cyclohexyl, cyclohexylmethyl, phenyl, benzyl, and tolyl acetoacetates, the corresponding ethylcarbonyl-, propylcarbonyl-, cyclohexylcarbonyl-, cyclobutylmethylcarbonyl-, phenylcarbonyl-, benzylcarbonyl-, and tolylcarbonylacetates, etc. Especially preferred β-keto esters are the methyl and ethyl acetoacetates.

The manner in which the β-keto ester is nitrosated to the 3-keto-2-oximino ester is not critical, and the nitrosation techniques already known to the art are satisfactory for use in the process. Such techniques include, e.g., the techniques taught in U.S. Pat. Nos. 2,844,630 (Johnson et al.) and 3,215,730 (Späthe et al.); Adams et al. *Organic Reactions*, Vol. 7, John Wiley & Sons, New York, pp. 327–377 (1953); Blatt, *Organic Syntheses*, Collective Vol. 2, John Wiley & Sons, New York, pp. 204–208; Baumgarten, *Organic Syntheses*, Collective Vol. 5, John Wiley & Sons, New York, pp. 32–35 and 373–375; and Adkins et al., *Journal of the American Chemical Society*, Vol. 60, pp. 1328–1331 (1938), the teachings of all of which are incorporated herein by reference. A nitrosation technique that has been found to be particularly suitable is the treatment of the β-keto ester with sodium nitrite and a strong acid, such as acetic acid.

The nitrosation step of the process results in the formation of a 3-keto-2-oximino ester which typically corresponds to the formula:

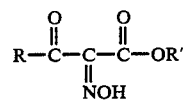

wherein R and R' have the same meanings as given above. This oxime is then converted to a protected 2-amine by any technique suitable for adding the desired protecting group, the particular technique not being critical since the objective is merely to convert the 2-oximino group to a protected amino group. Such techniques are already known and are disclosed, e.g., in Albertson et al., *Journal of the American Chemical Society*, Vol. 70, pp. 1150–1152 (1948); Baumgarten, *Organic Syntheses*, Collective Vol. 5, John Wiley & Sons, New York, pp. 373–378; Gross et al., *The Peptides*, Vol. 3, Academic Press, New York, especially pp. 7–49 (1981); and Degering, *An Outline of Organic Nitrogen Compounds*, University Lithoprinters, Ypsilanti, Mich., pp. 192–193 (1945), the teachings of all of which are incorporated herein by reference.

It is ordinarily preferred to accomplish the conversion to the protected 2-amine by simultaneously or consecutively reacting the oxime with hydrogen and an acid anhydride to convert the oxime to an amide group and thus form a compound generally corresponding to the formula:

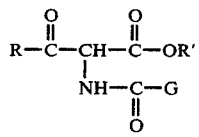

wherein R and R' have the same meanings as given above, and G is an alkyl, cycloalkyl, or aryl radical, generally such a group containing 1-10 carbons (e.g., the groups mentioned above as exemplary of the R and R' groups), and preferably an alkyl group containing 1-6 carbons. As is conventional in such reactions, it is usually desirable to conduct the hydrogenation step of the reaction in the presence of a hydrogenation catalyst, such as a nickel or palladium-on-carbon catalyst or one of the other catalysts known to be useful in such reactions. The particular acid anhydride employed in the reaction may be any anhydride capable of forming such an amido compound but is preferably acetic anhydride.

In another preferred embodiment of the invention, the oxime is reacted with hydrogen and an acid such as hydrochloric, perchloric, formic, or acetic acid, etc., suitably in the presence of a conventional hydrogenation catalyst, to form a compound corresponding to the formula:

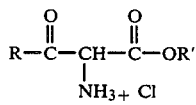

which is then reacted with a suitable amine protecting agent, such as benzylchloroformate, t-butylchloroformate, trityl chloride, trichloroacetyl chloride, or other compound corresponding to the formula ClCOOG, to form a product corresponding to the formula:

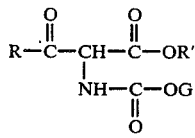

wherein R, R', and G have the same meanings as given above. This manner of converting the oxime to a protected 2-amine is apt to be preferred when it is desired to add a protecting group that decomposes in a hydrogen atmosphere and therefore cannot be added by the hydrogen/anhydride technique.

Regardless of the manner in which it is prepared, the protected 2-amine can then be reductively aminated by known techniques to form a 2-amido-3-aminocarboxylic acid ester which, in a preferred embodiment of the invention, is a compound corresponding to the formula:

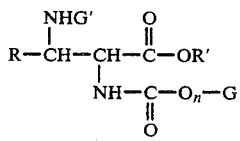

wherein R, R', and G have the same meanings as given above, n is zero or one, and G' is hydrogen or an alkyl, cycloalkyl, or aryl group which may be the same as or different from any or all of the R, R', and G groups but, like those groups, is generally selected from radicals containing 1-10 carbons. Unlike those other groups, however, the G' is preferably benzyl.

As is the case with the earlier steps of the process, the particular manner in which the reductive amination is conducted is not critical, and conventional techniques for conducting it may be employed. Suitable techniques are disclosed, e.g., in Borch et al., *Journal of the American Chemical Society*, Vol. 93, pp. 2895-2904 (1971); Blatt, *Organic Syntheses*, Collective Vol. 2, John Wiley & Sons, New York, pp. 503-506; and Horning, *Organic Syntheses*, Collective Vol. 3, John Wiley & Sons, New York, pp. 501-502 and 717-719, the teachings of all of which are incorporated herein by reference. Ordinarily the reduction mechanism employed in the process is catalytic reduction or the use of sodium cyanoborohydride, preferably the latter. As indicated by the above formula, the aminating reactant may be ammonia or any primary alkyl, cycloalkyl, or aryl amine capable of providing the —NHG' group, but it is generally preferred to employ ammonia or an amine, such as benzylamine, which contains a group that will be easily removable from the product to provide a free amino group in the 3-position.

When benzylamine is employed as the aminating agent, the 2-amido-3-aminocarboxylic acid esters corresponding to the above formula are novel compounds, the preferred compounds being those wherein R and R' are independently selected from methyl and ethyl, and —O$_n$—G represents methyl, t-butoxy, or benzoxy.

As indicated above, it is sometimes desirable to convert the 2-amido-3-aminocarboxylic acid ester to a compound containing a free carboxyl group and/or one or two free amino groups. These derivatives may be prepared by conventional techniques, e.g., the hydrogenation of any 3-benzylamino group to a primary amino group, suitably in the presence of a palladium-on-carbon or other hydrogenation catalyst, followed by the hydrolysis of the amido and ester groups to, respectively, amino and acid groups. Here again the particular technique used is not critical and can be any of the known techniques for conducting such hydrogenations and hydrolyses, e.g., the techniques disclosed in U.S. Pat. No. 3,394,187 (Markiewitz) and Allinger et al., *Organic Chemistry*, Worth Publishers, pp. 532-537 (1971), the teachings of which are incorporated herein by reference.

Prior to or after deprotection of any amino and/or carboxyl groups, the products may be purified to separate them into threo and erythro diastereomers.

The following examples are given to illustrate the invention and are not intended as a limitation thereof.

EXAMPLE I

Part A

A suitable reaction vessel was charged with 0.385 mol of ethyl acetoacetate and 0.87 mol of acetic acid and cooled in an ice bath. A solution of 0.435 mol of sodium nitrite in 50 ml of water was added dropwise to the reaction mixture over a period of about 30 minutes, and the resultant reaction mixture was stirred until its color went from clear to light orange. The ice bath was then removed and stirring continued for an additional two hours, another 140 ml of water being added 30 minutes into this two-hour stirring period. Work-up of the reaction mixture resulted in the isolation of ethyl 2-oximinoacetoacetate in a 95% yield.

Part B

A Parr flask was charged with 0.2 mol of ethyl 2-oximinoacetoacetate, 0.4 mol of acetic anhydride, 45 psi of hydrogen, and a mixture of 0.25 g of 5% palladium-on-carbon and 0.4 g of 10% palladium-on-carbon and shaken for about 22 hours. Work-up of the resultant reaction mixture provided a 92.3% yield of ethyl 2-acetamidoacetoacetate.

Part C

A dispersion of 0.204 mol of benzylamine in 100 ml of methylene chloride was cooled to 12° C. in an ice bath, and 0.199 mol of ethyl 2-acetamidoacetoacetate in 40 ml of methylene chloride was added thereto. The ice bath was then removed, and reaction was allowed to proceed for 440 minutes, after which the mixture was worked up to isolate ethyl 2-acetamido-3-benzylaminobutene-2-oate in an 81% yield.

Part D

A solution of 0.125 mol of sodium cyanoborohydride in 40 ml of methanol was added to a mixture of 0.162 mol of ethyl 2-acetamido-3-benzylaminobutene-2-oate and 100 ml of methanol. Another 30 ml of methanol were added, and 0.5 ml of 0.02% bromcresol was added to make the reaction mixture blue. The reaction mixture was cooled in ice as 2M HCl in methanol was added dropwise until the pH was determined to be 4.0 and then was stirred at room temperature for an additional three hours. After work-up, the yield of ethyl 2-acetamido-3-benzylaminobutyrate diastereomers was determined to be 96%.

EXAMPLE II

Repetition of Example I, Part B, except for substituting 0.65 g of 5% of palladium-on-carbon for the mixture of 0.25 g of 5% palladium on carbon and 0.4 of 10% palladium-on-carbon gave comparable results.

EXAMPLE III

A 50:50 mixture of 40 g of the threo and erythro diastereomers of ethyl 2-acetamido-3-benzylaminobutyrate was pulverized and stirred with 50 ml of ice cold ether/ethanol in a 4/1 (v/v) amount for 15 minutes, after which crystals of the threo diastereomer were collected by filtration and recrystallization from chloroform/ether to give white needles having a melting point of 96°–98° C. The solvent was removed from the mother liquor to give the erythro diastereomer as a clear oil.

EXAMPLE IV

Five grams of ethyl 2-acetamido-3-benzylaminobutyrate were dispersed in 20 ml of ethanol together with 0.5 of 5% palladium-on-carbon and shaken under 40 psi of hydrogen until hydrogen uptake had ceased. The mixture was filtered through Celite and evaporated to give a 100% yield of ethyl 2-acetamido-3-aminobutyrate.

EXAMPLE V

Five grams of ethyl 2-acetamido-3-aminobutyrate were dispersed in 10 ml of cold methanol, after which 1.51 g of potassium hydroxide in 15 ml of methanol were added. The mixture was stirred in an ice bath and then allowed to warm to 23° C. over a period of 18 hours. The solvent was removed at reduced pressure, and the residue was dissolved in a minimum of warm water and adjusted to a pH of 6.5 with hydrochloric acid. Upon cooling, crystals of 2-acetamido-3-aminobutyric acid were formed in a 95% yield.

EXAMPLE VI

Example V was repeated except that the starting material was ethyl 2-acetamido-3-benzylaminobutyrate. The reaction resulted in a 95% yield of 2-acetamido-3-benzylaminobutyric acid.

EXAMPLE VII

Five grams of ethyl 2-acetamido-3-aminobutyrate were refluxed in 50 ml of 6M HCl for 6 hours, after which the solvent was removed at reduced pressure. The residue was resuspended in water and evaporated to remove residual acid, followed by resuspension in a minimum of water and adjustment to a pH of 7 with 30% ammonium hydroxide. Collection by filtration provided a 95% yield of crystals of 2,3-diaminobutyric acid.

EXAMPLE VIII

Example VII was repeated except that the ethyl 2-acetamido-3-aminobutyrate was replaced with 3.1 g of 2-acetamidobutyric acid. The reaction again resulted in a 95% yield of crystals of 2,3-diaminobutyric acid.

EXAMPLE IX

A gram of 2-amino-3-benzylaminobutyric acid was dispersed in 10 ml of aqueous ethanol together with 0.1 g of 10% palladium-on-carbon and shaken under 40 psi of hydrogen until uptake of hydrogen had ceased. After evaporation of solvent, 10 ml of 1M HCl was added, and the mixture was evaporated. The residue was resuspended in a minimum of hot water and adjusted to a pH of 7 with 30% ammonium hyroxide to precipitate crystals of 2,3-diaminobutyric acid.

EXAMPLE X

Example VII was repeated except that ethyl 2-acetamido-3-benzylaminobutyrate was refluxed in 6M HCl to yield 2-amino-3-benzylaminobutyric acid.

EXAMPLE XI

Example VII was repeated except that 2-acetamido-3-benzylaminobutyric acid was refluxed in 6M HCl to yield 2-amino-3-benzylaminobutyric acid.

EXAMPLE XII

Part A

A solution of 0.054 mmol of ammonia in ethanol was added dropwise to 0.054 mol of ethyl 2-acetamidoacetoacetate in 40 ml of ice cold ethanol over a period of 10 minutes. The reaction vessel was tightly capped and allowed to stir overnight at 23° C., after which the solvent was removed at reduced pressure to provide ethyl 2-acetamido-3-aminobut-2-enoate in a 3/1 ratio of two geometrical isomers.

Part B

After dispersing 0.043 mol of ethyl 2-acetamido-3-aminobut-2-enoate in 25 ml of methanol together with 0.043 mol of sodium cyanoborohydride and a few drops of 0.04% bromcresol green indicator, the reaction mixture was cooled in ice, and 2M methanolic hydrochloric acid was added until the yellow color stabilized. The ice bath was removed, and the reaction was stirred for two hours, after which the solvent was removed and the reaction mixture worked up to provide ethyl 2-acetamido-3-aminobutyrate as a slightly greenish oil containing a 2.5/1 molar ratio of threo and erythro diastereomers.

EXAMPLE XIII

Part A

A dispersion of 0.031 mol of ethyl 2-oximinoacetoacetate, 0.93 equivalent of ethanolic hydrochloric acid, and 0.5 g of 10% palladium-on-carbon in 80 ml of absolute ethanol was shaken on a Parr apparatus under 40 psi of hydrogen. After uptake had ceased, the crude mixture was evaporated at reduced pressure, followed by dilution with and evaporation of ethanol to remove excess acid. Trituration with ether gave crystals which were recrystallized from ethanol/ether. The product was determined to be ethyl 2-aminoacetoacetate hydrochloride.

Part B

A solution of 1.25 mmol of ethyl 2-aminoacetoacetate in 1 ml of absolute ethanol was cooled in ice. Then 1.25 mmol of benzylchloroformate was added, followed by 1.5 mmol of sodium bicarbonate. After stirring for one hour, the mixture was evaporated to give crude ethyl 2-carbobenzoxyamidoacetoacetate.

It is obvious that many variations can be made in the products and processes set forth above without departing from the spirit and scope of this invention.

I claim:

1. A process which comprises (A) nitrosating a β-keto ester corresponding to the formula:

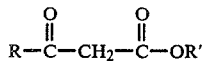

by treating it with sodium nitrite and a strong acid so as to form a 3-keto-2-oximino ester corresponding to the formula:

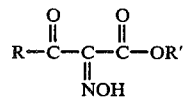

(B) converting the oximino ester to a protected 2-amine corresponding to the formula:

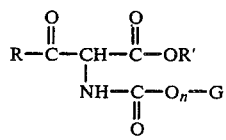

by (1) simultaneously or consecutively reacting it with hydrogen and an acid anhydride in the presence of a hydrogenation catalyst or (2) reacting it with hydrogen and an acid in the presence of a hydrogenation catalyst and then with a protecting agent corresponding to the formula ClCOOG, and (C) reductively aminating the 3-position of the protected 2-amine by reacting it with ammonia or a primary amine in the presence of sodium cyanoborohydride so as to form a 2-amido-3-aminocarboxylic acid ester corresponding to the formula:

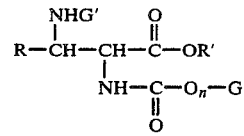

in which formulas R, R', and G are independently selected from alkyl, cycloalkyl, and aryl groups containing 1-10 carbons; G' represents hydrogen or an alkyl, cycloalkyl, or aryl group containing 1-10 carbons; and n is zero or one.

2. The process of claim 1 wherein R and R' are alkyl groups containing 1-6 carbons, G is benzyl or an alkyl group containing 1-6 carbons, and G' is hydrogen or benzyl.

3. The process of claim 2 wherein R, R', and G are independently selected from methyl and ethyl and n is zero.

4. The process of claim 2 wherein R and R' are independently selected from methy and ethyl, G is butyl or benzyl, and n is one.

5. The process of claim 1 wherein the oximino ester is converted to a protected 2-amine by simultaneously or consecutively reacting it with hydrogen and acetic anhydride in the presence of a hydrogenation catalyst.

6. The process of claim 1 wherein the oximino ester is converted to a protected 2-amine by reacting it with hydrogen and an acid selected from hydrochloric, perchloric, formic, and acetic acids in the presence of a hydrogenation catalyst and then with a protecting agent selected from benzylchloroformate, t-butylchloroformate, trityl chloride, and trichloroacetyl chloride.

7. The process of claim 6 wherein the acid is hydrochloric acid.

8. The process of claim 6 wherein the protecting agent is benzylchloroformate.

9. The process of claim 6 wherein the protecting agent is t-butylchloroformate.

10. A 3-benzylamino-2-amidocarboxylic acid ester corresponding to the formula:

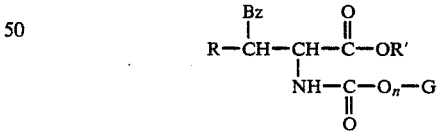

wherein Bz is benzylamino; R, R', and G are independently selected from alkyl, cycloalkyl, and aryl; and n is zero or one.

11. The 3-benzylamino-2-amidocarboxylic acid ester of claim 10 wherein R and R' are independently selected from methyl and ethyl, and $-O_n-G$ represents methyl, t-butoxy, or benzoxy.

12. The 3-benzylamino-2-amidocarboxylic acid ester of claim 11 wherein R and $-O_n-G$ are methyl and R' is ethyl.

* * * * *